United States Patent
Grove

(10) Patent No.: US 10,699,554 B2
(45) Date of Patent: *Jun. 30, 2020

(54) INTERACTIVE MEDIA DEVICE

(71) Applicant: ESCO Technologies, LLC, Liberty Township, OH (US)

(72) Inventor: Jerry Grove, Liberty Township, OH (US)

(73) Assignee: ESCO Technologies, LLC, Liberty Township, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/448,661

(22) Filed: Jun. 21, 2019

(65) Prior Publication Data

US 2019/0311602 A1    Oct. 10, 2019

Related U.S. Application Data

(63) Continuation of application No. 16/119,225, filed on Aug. 31, 2018, now Pat. No. 10,339,790, which is a continuation of application No. 15/171,295, filed on Jun. 2, 2016, now Pat. No. 10,068,460.

(60) Provisional application No. 62/171,234, filed on Jun. 4, 2015.

(51) Int. Cl.
| | |
|---|---|
| *G08B 25/01* | (2006.01) |
| *G08B 25/10* | (2006.01) |
| *G08C 17/02* | (2006.01) |
| *H04N 21/478* | (2011.01) |
| *H04N 21/422* | (2011.01) |
| *G16H 10/60* | (2018.01) |
| *G06Q 50/00* | (2012.01) |
| *G06F 19/00* | (2018.01) |

(52) U.S. Cl.
CPC .......... *G08B 25/016* (2013.01); *G06F 19/00* (2013.01); *G06Q 50/00* (2013.01); *G08B 25/10* (2013.01); *G08C 17/02* (2013.01); *G16H 10/60* (2018.01); *H04N 21/4221* (2013.01); *H04N 21/478* (2013.01); *G08C 2201/90* (2013.01)

(58) Field of Classification Search
CPC ...... G08B 25/016; G08B 25/10; G16H 10/60; G06Q 50/00; G08C 17/02; G08C 2201/90; H04N 21/4221; H04N 21/478
See application file for complete search history.

(56) References Cited

U.S. PATENT DOCUMENTS

| | | | |
|---|---|---|---|
| 5,534,851 A | 7/1996 | Russek | |
| 8,098,153 B2 | 1/2012 | Kraus et al. | |
| 8,326,649 B2 | 12/2012 | Rosenfeld | |
| 9,253,514 B2 | 2/2016 | Magri et al. | |

(Continued)

*Primary Examiner* — Mohamed Barakat
(74) *Attorney, Agent, or Firm* — Thomas E. Lees, LLC

(57) ABSTRACT

An interactive media device comprises a remote control interface that receives a wireless signal from a corresponding remote control with an emergency button. A controller decodes the wireless signal to determine if the user has pressed a button of the remote control to operate an associated television or if the user has pressed the emergency button on the remote control. If the user has pressed a button of the remote control to operate the associated television, then a television interface that issues an instruction based on the wireless signal to the associated television. However, if the user has pressed the emergency button, a medical emergency interface that issues an alert to a local or remote response unit.

20 Claims, 5 Drawing Sheets

(56) References Cited

U.S. PATENT DOCUMENTS

| | | |
|---|---|---|
| 9,305,450 B2 | 4/2016 | Halverson et al. |
| 2005/0151640 A1 | 7/2005 | Hastings |
| 2008/0004904 A1 | 1/2008 | Tran |
| 2008/0229352 A1* | 9/2008 | Pino ................. G06Q 30/02 725/22 |
| 2010/0205636 A1* | 8/2010 | Coburn ............. H04N 5/44543 725/46 |
| 2011/0199214 A1 | 8/2011 | Gawlick |
| 2011/0255670 A1 | 10/2011 | Seidberg et al. |
| 2014/0049696 A1 | 2/2014 | Sirpal et al. |
| 2014/0178846 A1* | 6/2014 | Letzt ..................... G09B 5/06 434/308 |
| 2015/0054631 A1* | 2/2015 | Hayes ................... G08C 17/02 340/12.28 |
| 2015/0121412 A1 | 4/2015 | McRae |
| 2015/0296245 A1* | 10/2015 | Toh ....................... G08C 17/02 725/80 |
| 2016/0012702 A1 | 1/2016 | Hart et al. |
| 2016/0029082 A1* | 1/2016 | Wordley ............. H04N 21/454 725/52 |

\* cited by examiner

INTERACTIVE MEDIA DEVICE

CROSS REFERENCE TO RELATED APPLICATIONS

This application is a continuation of U.S. patent application Ser. No. 16/119,225, filed Aug. 31, 2018, entitled INTERACTIVE MEDIA DEVICE, now allowed, which is a continuation of U.S. patent application Ser. No. 15/171,295, filed Jun. 2, 2016, entitled INTERACTIVE MEDIA DEVICE, now issued as U.S. Pat. No. 10,068,460, which claims the benefit of U.S. Provisional Patent Application Ser. No. 62/171,234, filed Jun. 4, 2015, entitled INTERACTIVE MEDIA DEVICE, the disclosures of which are hereby incorporated herein by reference.

BACKGROUND

The present disclosure relates to electronic systems that function as an interface between a user and distributed media resources, including entertainment resources, communication resources, medical resources, and informational resources.

As technology advances, it is becoming more difficult for select demographics of individuals to access, use, and enjoy the benefits of media sources, such as those available over the Internet, via television, telephone, etc. For instance, the elderly, disabled individuals, and persons receiving physical therapy may all have limitations that affect their enjoyment of conventional media products. Moreover, economic realities limit the ability of many individuals to thoroughly enjoy available media sources, including access to the Internet, television, telephone, etc.

BRIEF SUMMARY

According to aspects of the present disclosure, an interactive media device is disclosed. The interactive media device, which can be implemented for example, in the form factor of a set-top box, comprises a remote control interface, a medical emergency interface, a television interface, and a network interface. The remote control interface receives wirelessly transmitted signals from a corresponding remote control. Moreover, the remote control interface is configured to receive a first wireless command issued from the remote control in response to a user selection of an emergency button on the remote control, and a second wireless command issued from the remote control in response to the user selection of at least one television station selection button on the remote control.

The medical emergency interface issues an alert over the network to a medical response unit, where the alert is issued responsive to receipt of the first wireless command by the remote control interface.

The television interface issues instructions to an associated television receiver to select a channel according to previously programmed favorite channel options, responsive to receipt of the second wireless command by the remote control interface.

The network interface communicably couples the device to a remote media service provider via a network, wherein the network interface enables the remote media service provider to program customized functionality of the alert by the medical emergency interface and customized television channel options of the television interface of the device on behalf of a user.

According to further aspects of the present disclosure, a device comprises a remote control interface, a medical emergency interface, a television interface, a network interface, a monitor interface, and a controller. The remote control interface receives wirelessly transmitted signals from a corresponding remote control. Moreover, the remote control interface is configured to receive a first wireless command issued from the remote control in response to a user selection of an emergency button on the remote control, and a second wireless command issued from the remote control in response to the user selection of at least one television station selection button on the remote control.

The medical emergency interface issues an alert over the network to a medical response unit, where the alert is issued responsive to receipt of the first wireless command by the remote control interface.

The television interface issues instructions to an associated television receiver to select a channel according to previously programmed favorite channel options, responsive to receipt of the second wireless command by the remote control interface.

The network interface communicably couples the device to a remote media service provider via a network. The network interface enables the remote media service provider to program customized functionality of the device for the user, including programming the alert and programming the favorite channel options on behalf of a user.

The monitor interface electronically communicates across the network via the network interface.

The controller is connected to the remote control interface, the medical emergency interface, the television interface, the network interface, and the monitor interface, to control operation of the device.

According to yet further aspects of the present disclosure, a device comprises a remote control interface, a controller, a television interface, a medical emergency interface, and a network interface. The remote control interface receives a wireless signal from a corresponding remote control, the remote control having an emergency button that upon actuation, causes the remote control to issue a first wireless command as the wireless signal.

The controller is electronically connected to the remote control interface. The controller decodes a representation of the wireless signal received by the remote control interface to determine select one of whether the user has pressed the emergency button by identifying the first wireless command, and whether a user has pressed a button of the remote control to control an associated television.

The television interface is electronically connected to the controller. The television interface issues an instruction to the associated television in response to the controller determining that the user has pressed a button of the remote control to control the associated television. The instruction is based on a translation of the wireless signal to a corresponding television adjustment command.

The medical emergency interface is also electronically connected to the controller. The medical emergency interface issues an alert in response to the controller determining that the user has pressed the emergency button.

The network interface communicably couples the device to a remote media service provider via a network. The network interface enables a remote media service provider to access the device and program customized functions of the device on behalf of the user.

DETAILED DESCRIPTION

According to various aspects of the present disclosure, systems, and computer implemented processes are provided, which facilitate a user-friendly, interactive interface between a user and distributed media resources, including entertainment resources, communication resources, medical resources, and informational resources. More particularly, an interactive media device is provided, (e.g., which may take the form factor of a television set-top box), that serves as a media aggregator. For instance, the interactive media device serves as a user interface, connecting local hardware technologies, which may include television, telephone, remote control, medical and other monitoring devices, etc., to a computer network. In this regard, the interactive media device forms a special purpose processing device that is distinct and different from a general purpose computer.

The interactive media device also connects remote resources to the user, e.g., via network access. Example resources include television programming, telephone services, Internet browsing, medical resources, etc. Still further, support, maintenance, programming of capabilities and features, and other services can be administered remotely, e.g., from a suitable service provider. Also, in addition to aggregating media resources, the content is organized and presented in a manner facilitating an enjoyable user experience when interacting with the interactive media device. Still further, support can be provided in a robust manner, facilitating a concierge for technology needs of the users.

In this manner, aspects of the present disclosure improve technologies including machine-to-machine control and interfacing, and wireless-to-Internet bridging. In particular, aspects herein address the technical problem integrating multiple, distinct and independent media systems into a single, hand-held wireless remote that interacts with an interactive media device. The technical problem is solved with a technical solution that provides a controller in a single interactive media device that interacts with the wireless remote control to manage independent media streams. The technical solution herein brings about multiple technical effects, including automated health metric integration and conveyance in a media delivery platform that is easy to operate, and that can be remotely managed.

Figure 1:
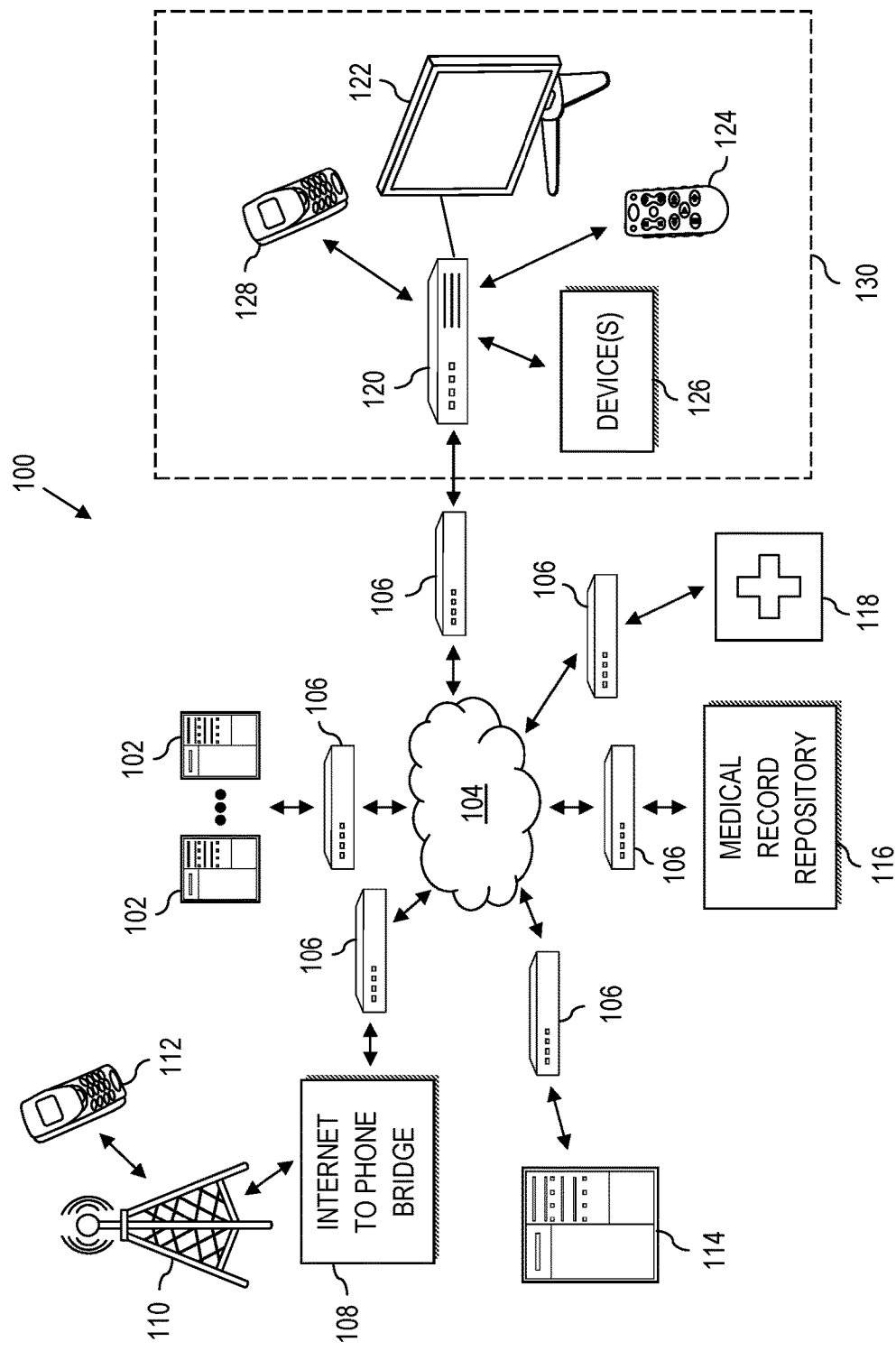
FIG. 1 is a block diagram of a system that provides interactive media to an interactive media device, according to aspects of the present disclosure herein.

System Overview:

Referring now to the drawings and in particular to FIG. 1, a general diagram of a computer system 100 is illustrated according to various aspects of the present disclosure. The illustrated computer system 100 is a special purpose (particular) system that operates using media devices that link users to media resources that are distributed throughout local environments and throughout remote environments. The media resources can include physical hardware devices, software executing on one or more physical hardware device(s), information, and other forms of media, as set out in greater detail herein.

The computer system 100 comprises a plurality of hardware processing devices (designated generally by the reference 102) that are linked together by one or more network(s) (designated generally by the reference 104). In general, a processing device 102 can be implemented as a transactional system, purpose-driven appliance, special purpose computing device and/or other device capable of communicating over the network 104. Other types of processing devices 102 include for example, personal data assistant (PDA) processors, palm computers, cellular devices including cellular mobile telephones and smart telephones and tablet computers. The processing devices 102 can also comprise netbook computers, notebook computers, personal computers and servers.

The network(s) 104 provides communications links between the various processing devices 102 and may be supported by networking components 106 that interconnect the processing devices 102, including for example, routers, hubs, firewalls, network interfaces, wired or wireless communications links and corresponding interconnections. Moreover, the network(s) 104 may comprise connections using one or more intranets, extranets, local area networks (LAN), wide area networks (WAN), wireless networks (WiFi), the Internet, including the world wide web, cellular and/or other arrangements for enabling communication between the processing devices 102, in either real time or otherwise (e.g., via time shifting, batch processing, etc.).

In this regard, certain processing devices 102 provide resources available across the network 104 (e.g., the Internet). By way of example, certain processing devices 102 can serve as media resources (e.g., by hosting websites that provide access to television programming (e.g., satellite dish), online shopping, email and messaging, online information, and other sources of content), as will be described in greater detail herein.

In certain implementations, the network 104 also supports telephone/network conversion technologies. For instance, as illustrated, an Internet to phone bridge 108 converts signals between communications systems 110 (including corresponding devices 112 such as land-line telephones and/or cellular/smart telephones), and the network 104. For instance, the Internet to phone bridge 108 can convert between cellular, PBX, public switched telephone network (PSTN), etc., and TCP/IP or other desired network protocol. This ability facilitates communication using voice over Internet protocol (VOIP) and other technologies for voice-based communication.

The system 100 also includes a media service provider 114. The media service provider 114 is a special type of processing device 102, e.g., a server-based system (e.g., a web server, file server, and/or other processing device, combinations thereof, etc.) that supports interactive media devices, e.g., through subscription services to content. Content can include for example, one or more of television programming, telephone services, access to the network 104 (including the Internet), access to concierge services (e.g., support for the technology needs of users), access to medical resources and other forms of media, and access to a digital video recorder (DVR). The media service provider 114 also performs administrative, programming, and support services necessary to support interactive media devices and users of interactive media devices, as will be described more fully herein.

Also, the system 100 includes a particular type of processing device 102 implemented as a medical records repository 116, which communicates with other processing devices 102 across the network 104. For instance, the medical records repository 116 may be implemented as a cloud based service provider that stores, maintains, and collects at least one of medical data, clinical data, and health data, about individuals. The data can come from multiple sources, including the user, from one or more health providers, etc. In practice, there may actually be multiple medical records repositories 116 in communication with the system 100.

Still further, the system 100 includes a particular type of processing device 102 implemented as a medical response unit 118, which communicates with other processing devices 102 across the network 104. The medical response unit 118 is a processing device that communicates with the interactive media devices as will be set out in greater detail herein for emergency situations. For instance, the medical response unit 118 may comprise a communication device at a nurse station, hospital, emergency response unit, local care provider, health monitoring company, etc. Moreover, the communication between an interactive media device and the medical response unit 118 may cross multiple domains, such as the Internet, cellular, telephone, etc.

Moreover, the system 100 includes an interactive media device 120. Although only one instance of the interactive media device 120 is shown for clarity and conciseness of discussion, in practice, each subscriber of the media service provider 114 would have at least one interactive media device 120. The interactive media devices 120 provide the user interface to the system 100. For instance, as illustrated, the interactive media device 120 communicates with other processing devices 102 (including the internet to phone bridge 108, media service provider 114, medical record repository 116, medical response unit 118, etc.) across the network 104.

The interactive media device 120 also communicates with local hardware devices. For instance, the interactive media device couples locally to a television 122. This allows television programming, including high definition television, satellite programming, pay-per-view programming, and other sources of viewing content to be communicated from a content provider (including a network based content provider), e.g., one of the processing device 102 to the television 122 (e.g., to provide IP based television). In this regard, the interactive media device 120 can also communicate with other television devices, such as a satellite dish, digital video recorder, etc.

The interactive media device also communicates a remote control 124. The remote control 124 provides numerous specific features, including features not typical of remote controls. For instance, the remote control 124 includes a nurse call button that interfaces through the interactive media device 120 to contact a suitable medical response unit 118. The specific routing of information in response to pressing the nurse call button will depend upon the specific application. By way of example, in an assisted living community, the nurse call button may trigger a local, on-site nurse or other emergency response technician to attend to the individual. The nurse call button may also contact relatives, doctors, emergency responders, local law enforcement, or other desired source that receives a communication from the medical response device 118.

For instance, in an example implementation, the interactive media device 120 includes memory and a rules engine that controls who is contacted in response to actuation of the nurse call button. In further examples, such memory and rules can be stored remotely, e.g., in a data storage device hosted by the media service provider 114.

The interactive media device 120 can also communicate with a monitoring device 126. For instance, in certain implementations, individuals have vital information collected locally, e.g., based upon wired or wireless weight scales, heart rate monitors, glucose monitors, or other device(s). Such monitoring device(s) 126 communicate via wired or wireless connection to the interactive media device 120, which can communicate the collected data to a corresponding resource, such as the medical record repository 116. As such, updated locally monitored or measured information, e.g., clinical and health based information, is collected and maintained in an up to date, and integrated manner.

Moreover, the medical record repository 116 or other processing device of the system 100 can push information, commands, instructions or other information back to the interactive media device 120 and/or monitoring device(s) 126. For instance, the interactive media device 120 can receive push notifications for display on the television 122, e.g., reminders to take medications, announcements of incoming telephone calls, emails, or other communications, play back rehabilitation or exercise videos from a health provider communicating across the network 104, etc.

The interactive media device 120 can also communicate with a local telephone 128. This allows a local telephone 128 (e.g., landline, cellular, etc.), to communicate over the internet, e.g., via VOIP using the internet to phone bridge 108 or other suitable technology.

Yet further, the interactive media device 120 can provide other features, such as onscreen caller ID, by combining capability of a telephone interface with a television interface. Also, the interactive media device 120 can include hearing impaired capability, such as voice mail transcription capabilities.

The television 122 may be any standard television with a channel receiver and speakers and can be controlled by a signal from the interactive media device 120 (via the remote control 124) to change channels, volume, etc. The signal from the interactive media device 120 to the television 122 may be wired or wireless (e.g., RF, infrared, Bluetooth, ZigBee, etc.). Further, the television 122 may include additional features such as a built-in digital video recorder (DVR), and the signal from the interactive media device 120 may control the DVR as well. On the other hand, the television 122 may merely be a display with or without speakers. In this case, the television 122 just displays video from a video feed supplied to the television 122 via a signal from the interactive media device 120. Further, if the television has speakers, then the television may emit audio from an audio input supplied to the television 122 via the signal from the interactive media device 120. Thus, the television 122 may range from a display device to a full-fledged television with built in accessories. Various combinations of the interactive media device 120, the television 122, the remote control 124, the monitoring device(s) 126, and the telephone 128 may be used to implement an interactive media system 130.

Moreover, the features and capabilities of the interactive media device 120 are setup, controlled, programmed, or otherwise maintained by the media service provider server 114. For instance, a representative at the media service provider 114 can reset the interactive media device 120, change, alter, update, downgrade, provide content or messaging to, etc., the interactive media device 120. In certain applications, the media service provider 114 can access features of the interactive media system 130 down to the remote control 124 and other features of the interactive media system 130.

Still further, the interactive media device 120 includes a controller that implements a graphical user interface that can be displayed on the television 122. The graphical user interface allows the user to navigate the features made available by the media service provider server 114. For instance, a user can interact via the graphical user interface for selecting and using available features, including television programming, on-line communication (e.g., e-mail, messaging, etc.), website browsing, Internet searching, medical/clinical interactions, and other capabilities controlled through the interactive media device 120. In this regard, the media service provider 114 can control the graphical user interface to make the available capabilities of the interactive media interface easy for the operator to navigate and use, e.g., by setting appropriate fonts, font size, organization, control flow, etc.

In an example implementation, a customized graphical user interface provides menus that the user can navigate to access media provided through the media service provider 114. For instance, a user navigates a set of icon-based menu items to watch television, place telephone calls by combining telephone and television capabilities or access network based resources. Network based resources can include access entertainment, preconfigured options to discover features happening around the user's community, browse community services, browse community dining and food, interact with a calendar, set up calendar based reminders, e.g., for birthdays, anniversaries, appointments, etc., schedule personal care appointments (e.g., hair appointments, dry cleaners, etc.), discover educational resources, browse the Internet, send emails or otherwise communicate, access social media, etc.

Moreover, the graphical user interface can provide a virtual (graphical) version of the emergency nurse call button (e.g., to communicate with the medical response unit 118).

Still further, the graphical user interface can provide predetermined sets of information to the user, such as time, date, weather, temperature, etc. Moreover, the graphical user interface can provide recommendations to the user of the interactive media device 120, e.g., to recommend restaurants, programming, shopping, etc. For instance, the controller of the interactive media device 120 can include a processor coupled to memory that executes computer code to implement a web browser that supports queries, which can be preprogrammed or customizable through the graphical user interface, e.g., by interacting with the interactive media device 120 using a suitable input device, e.g., a keyboard, the remote control, etc.

Yet further, in certain implementations, the graphical user interface can provide a direct communication path to the media service provider 114, e.g., to upgrade, downgrade, change, services and features, get technical support, concierge services, help, medical help or other resources.

Example Interactive Media Device

According to aspects of the present disclosure, an interactive media device comprises a controller, a remote control interface, a television interface, and a medical emergency interface. The remote control interface receives a wireless signal from a corresponding remote control. In this example configuration, the remote control is a special controller that includes an emergency button. Upon user actuation of the emergency button, the remote control issues a wireless signal having a first wireless command embedded therein. That is, the remote control issues the first wireless command as the wireless signal, which is received by the remote control interface of the interactive media device.

Additionally, the controller is electronically connected to the remote control interface. The controller decodes a representation of the wireless signal received by the remote control interface to determine whether the user has pressed the emergency button by identifying the first wireless command, or whether a user has pressed a button of the remote control to control an associated television.

The interactive media device also includes a television interface electronically connected to the controller. Here, the television interface issues an instruction to the associated television in response to the controller determining that the user has pressed a button of the remote control to control the associated television. In this example configuration, the instruction is based on a translation of the wireless signal to a corresponding television adjustment command. Moreover, a medical emergency interface is electronically connected to the controller. The medical emergency interface issues an alert in response to the controller determining that the user has pressed the emergency button.

In an example configuration, assume the controller determines that a user has pressed a button of the remote control to control the television. In response thereto, the controller is operative to map the wireless signal received by the remote control interface into an analogous instruction to control the television. The instruction is then communicated from the controller to the television interface.

Moreover, the device includes an emergency medical record interface (e.g., in addition to or in lieu of the medical emergency interface) that is electronically connected to the controller. In this configuration, the emergency medical record interface further electronically communicates with an emergency medical record repository. In this configuration, the controller is operative to implement upon command, operations to cause medical record information to be extracted from the emergency medical record repository via the emergency medical record interface for presentation on a display screen of the associated television via the television interface.

Figure 2:
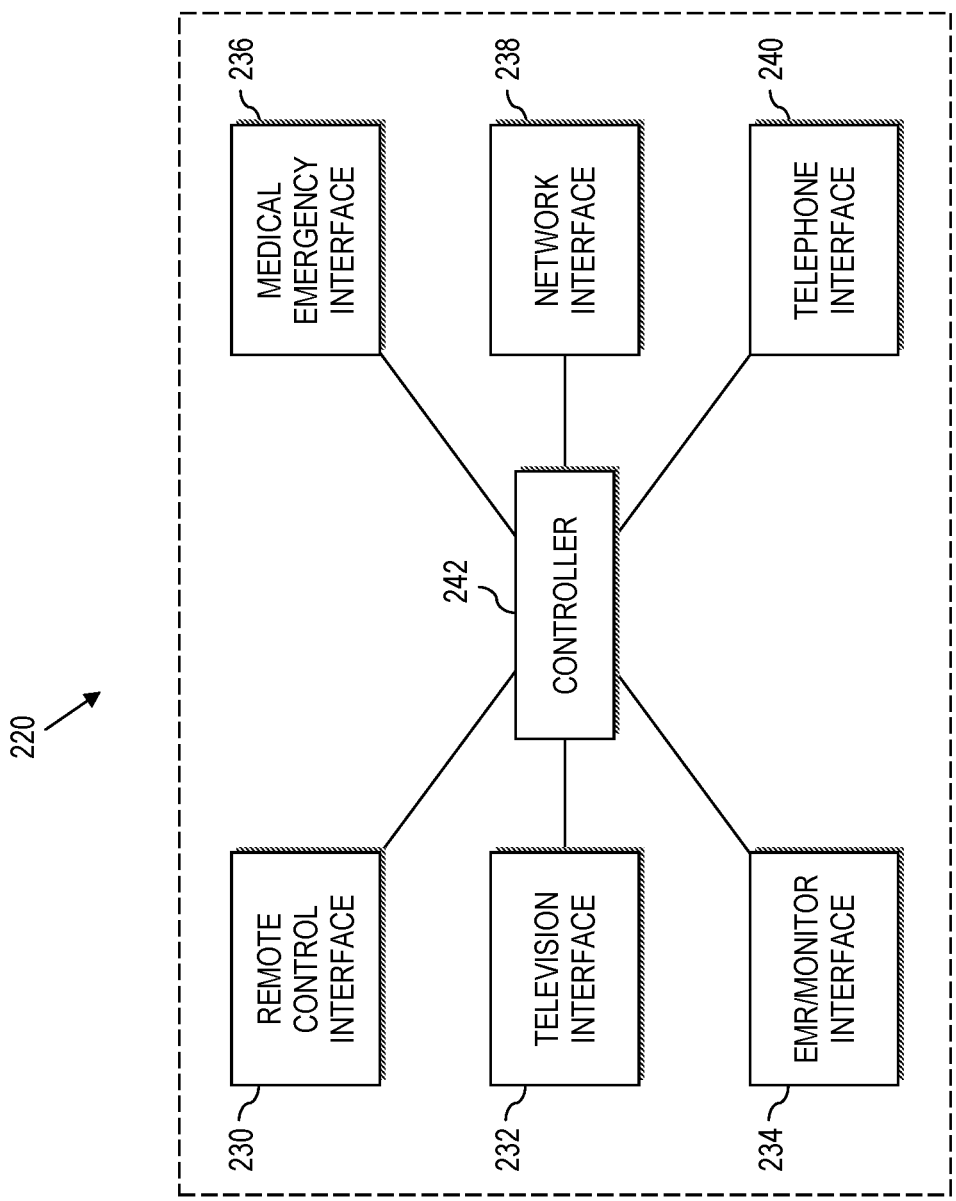
FIG. 2 is a block diagram of a device that serves as an interactive media device, according to aspects of the present disclosure herein.

Turning now to FIG. 2, a block diagram shows an example implementation of the interactive media device 220. The interactive media device 220 includes all of the features and capabilities of the interactive media device 120 of FIG. 1. As such, the disclosure of the interactive media device 120 is applicable to the interactive media device 220 of FIG. 2.

As shown, the interactive media device 220 comprises several optional interfaces: a wireless remote control interface 230, a television interface 232, a monitor interface 234 (also referred to herein as an emergency medical resource (EMR) interface, a medical emergency interface 236, a network interface 238, and a telephone interface 240 (wired, cellular, or both). The interactive media device 220 also includes a controller 242, which is electronically connected, and thus communicably coupled, to each of the wireless remote control interface 230, television interface 232, monitor interface 234, medical emergency interface 236, network interface 238, and telephone interface 240. Other interfaces may also be provided, e.g., depending upon the local and/or remote communication strategies that are deployed. Moreover, the interfaces described more fully herein include logical interfaces configured such that the functionality of the interactive media device 220 can be fully explained in the description herein. In practice, two or more interfaces may be integrated and/or share one or more hardware components. Moreover, in practical implementations, an interactive media device 220 can be implemented with any combination of one or more of the described interfaces.

Remote Control Interface

The remote control interface 230 receives a wireless signal from the remote control (124, FIG. 1). Any wireless protocol may be used to transmit the signal from the remote control to the remote control interface 230 (e.g., infrared, radio, Bluetooth, ZigBee, etc.). Regardless, the remote control interface 230 includes the necessary physical hardware to communicate with, e.g., receive commands from the associated remote control. The remote control interface 230 includes hardware circuitry necessary to buffer, store, and communicate representations of the received remote control commands to the controller 242.

In an example implementation, each button on the remote control is mapped to at least one wireless signal having a value corresponding to a wireless command. In example configurations, each function on the remote control maps to a different and unique value of the wireless signal. Moreover, the controller understands the mapping between the wireless signal values and the corresponding remote control functions. As such, the controller 242 can properly decode representations of wireless signals corresponding to button actuations on the remote control, and convert the decoded representations into corresponding actions by the interactive media device 220.

For instance, after receiving the signal, the remote control interface 230 passes a representation of the signal to a controller 242. Even though the controller 242 is shown as a separate stand-alone entity within the interactive media device 220, the controller 242 may be distributed among one or more of the several interfaces of the interactive media device 220 as described herein.

The controller 242 receives the signal from the remote control interface 230 and determines where the signal should be routed. For example, the controller 242 may determine whether a user has pressed a button of the remote control to operate the television (122 of FIG. 1). If so, then the controller 242 routes the signal to the television interface 232, which converts the signal to an instruction and issues the instruction to the television.

For example, if the user presses a "Volume Up" button on the remote control, then the remote control interface 230 receives the signal from the remote control and sends a representation of the signal to the controller 242, which determines that the signal is for the television. As such, the controller routes the signal to the television interface, which converts the signal to the appropriate volume up command in this example.

Television Interface

In certain implementations, the television interface 232 includes physical hardware that enables communication with the controller 242. Moreover, the television interface 232 includes hardware that integrates with a television, e.g., via a wired or wireless connection. For instance, in an example configuration, the television interface 232 includes a channel receiver (e.g., compatible with cable, satellite or other forms of television programming), which may be used with television screens that do not include their own channel receivers. The television interface 232 can also include an input to a television screen that bypasses an internal channel receiver. Still further, the television interface 232 may not include a channel receiver.

For instance, programming may be provided by another source, such as a satellite dish and separate receiver, etc. In such a case, when the user adjusts the channel to be displayed on the television screen, the television interface 232 supplies a direct video signal (and possibly an audio signal) for display on the television. Moreover, the channel receiver of the television interface 232 may be programmed to skip undesired channels so the user may cycle through only a set of user-favorited channels, as will be described with reference to FIG. 4. Still further, the television interface 232 may also include a DVR or other features necessary to communicate television programming to the television 122. Alternatively, the television interface can be configured to send commands to the associated television where all audio and receiver functions of the television are handled outside of the interactive media device 220. For instance, the television interface 232 can function as a passthrough of commands from the remote control to the television, of the television interface 232 can function as a converter, e.g., by converting between infrared, Bluetooth, etc., to bridge the television to the remote control.

Monitor Interface

The monitor interface 234 includes hardware that enables communication with the controller 242. Moreover, the monitor interface 234 communicably couples to local monitoring device(s) (see monitoring device 126 of FIG. 1) and can optionally communicate with the remote EMR repository (116, FIG. 1). For example, if the user is hooked up to a heart monitor (i.e., an EMR-based monitoring device 126), then the heart monitor may send a wired or wireless signal to the monitor interface 234 with information about the user's heart rate. Accordingly, the monitor interface 234 includes hardware such as a Bluetooth interface, connectors, or other necessary hardware to integrate with corresponding monitoring device(s). The monitor interface 234, the controller 242, or both can take responsibility to decode a signal received from an attached monitoring device 126.

The monitor interface 234 sends collected information, along with metadata (e.g., timestamp, user ID, etc.), to the EMR repository (116, FIG. 1). In certain implementations, the EMR repository is stored locally, in a memory device accessibly to the interactive media device 220. Additionally, or in lieu of the above, the EMR repository can be stored remotely, e.g., across the Internet. Here, the monitor interface 234 interface can communicate through the network interface 238 to translate information to network packets. In yet a further example, the collected information can be communicated to a remote EMR repository via the telephone interface 240.

In an illustrative example, the monitor interface 234 couples to an emergency medical record repository so as to be able to access medical records pertaining to the user. The monitor interface receives a medical record from the emergency medical record repository via the network interface 238. The controller 242 then causes the television interface 232 to override the content on the screen of the television to display the record on the television.

In other example configurations, the monitor interface 234 may request and receive medical information from the EMR repository (116, FIG. 1) or other suitable source. For example, if a user must take a certain medication at noon, then the EMR repository (e.g., medical record repository 116 of FIG. 1, media service provider 114 of FIG. 1, or other source) can dispatch information, such as in the form of an alert to take the medication to the interactive media device 220. The monitor interface 234 receives the medical information (directly, through the network interface 238, or the telephone interface 240). The monitor interface 234 may decode the medical record, whereupon the controller 242 routes the alert to the television interface 232, which overrides the signal to the television to display the alert (i.e., the medical information) to the user. Once the user sees the reminder to take the medication, the user may perform an action to indicate that the user has taken the medication (e.g., by pressing a menu button on the remote control and navigating to a completion screen). Where implemented, the indication is received by the interactive media device 220 and can be sent to an appropriate destination, e.g., to the EMR repository (e.g., medical record repository 116 of FIG. 1).

As another example, a source having an EMR repository, e.g., medical record repository 116 of FIG. 1 such as a doctor office, health website application, wellness center, rehabilitation facility, etc., may send a notification indicating that the user should step onto a scale for weighing. A user may also proactively decide to step on the scale. In this regard, the scale is a monitoring device 126 of FIG. 1. As described above, a message is displayed on the television, e.g., via the television interface 232, which instructs the user to step onto the scale. In this example, the scale has a Bluetooth connection to the monitor interface 234. As such, once the user steps onto the scale, the scale transmits a signal to the interactive media device 220 that the user has performed the action. The scale (or other monitoring device 126) can also send other information, e.g., measurements, readings, etc. In certain implementations, the interactive media device 220 sends an indication to a destination, such as an EMR repository via the monitor interface 234, that the user completed the action.

In yet another example, a source sends information to the interactive media device 220 indicating that the user should perform a rehabilitation exercise. In this case, the source may also send a video of the rehabilitation exercise, e.g., across the internet, which is received by the interactive media device 220, such as via the network interface 238, which is displayed on the television screen via the television interface 232 to guide the user in the rehabilitation process. Further, if the television interface 232 includes a DVR, the television interface 232 may automatically start recording the current channel while the rehabilitation exercise video is being played, so the user does not miss a portion of the regularly scheduled television program. Moreover, if the user is watching a prerecorded program on the DVR when the rehabilitation exercise video is available, the television interface may pause the prerecorded program so the user does not lose his/her place in the program.

In a still further example, a medical professional (e.g., nurse, doctor, therapist, etc.) may request the user's medical records through the EMR interface (e.g., by pressing a menu button on the remote control and navigating to a screen to request medical records). Then the EMR repository sends the records to the interactive media device 220 as described more fully herein, for display on the television by overriding the television as described above.

As a few non-limiting but illustrative examples of the use of the monitor interface 234, the following examples are provided. In one illustrative implementation, the interactive media device 220 electronically couples to at least one local medical device. Here, the interactive media device 220 receives medical information about the user via at least one local medical device and, sends the medical information about the user to the emergency medical record repository, e.g., via the network interface 238 or directly via the monitor interface 234.

In a further example implementation, the monitor interface 234 receives a medical record from the emergency medical record repository. In this example, the received medical record indicates that the user should perform a task. In response thereto, the controller 242 orchestrates with the television interface 232. In response, the television interface overrides the television to display the task on the television. Moreover, the monitor interface 234 can send an indication to the emergency medical record repository that the task has been completed based on feedback from the user. In a further example implementation, the monitor interface 234 couples to a local medical device. Assume a received medical record indicates that the user should perform a task using the local medical device. Here, the controller 242 coordinates with the television interface 232. In response, the television interface 232 overrides the television to display the task on the television and the monitor interface 234 sends an indication to the emergency medical record repository that the task has been completed based on feedback from the local medical device.

Also, in a particular implementation, a monitor interface 234 is electronically connected to the controller 242, where the monitor interface 234 couples to an emergency medical record repository 116 (FIG. 1) so as to be able to access medical records pertaining to a user. By way of illustration, the controller 242 further implements a graphical user interface for the display of information on the screen of the associated television. In an example embodiment, the graphical user interface is configured to provide a graphical version of the emergency button on the remote control, which when virtually actuated, causes the controller to issue an alert through the medical emergency interface. However, a virtual emergency button is not required in all implementations.

More particularly, the monitor interface 234 receives a medical record from the emergency medical record repository via the network interface. The controller 242 then coordinates with the television interface 232. In response thereto, the television interface 232 overrides the content on the screen of the television to display the record on the television.

Medical Emergency Interface

In certain implementations, the controller 242 determines whether the user has pressed an emergency button (e.g., a nurse call button) on the remote control. If so, then the controller 242 routes the signal to the medical emergency interface 236, which issues an alert based on the signal as described more fully with regard to FIG. 1. The medical emergency interface thus includes physical hardware necessary to communicate with the controller 242, and also to communicate to at least one medical response unit. This may be as simple as having a hardware necessary to sound a buzzer, turn on a light, initiate an alarm, etc. In more complex configurations, such as may be present in hospitals, nursing homes, assisted living communities, etc., the medical emergency interface 236 includes hardware necessary to interface with corresponding emergency call/response systems. Alternatively, and/or additionally, the medical emergency interface 236 can trigger actions to communicate over the Internet (e.g., via the network interface 238), make automated telephone calls (e.g., via the telephone interface 240), etc.

For example, if the interactive media device 220 is located in a nursing home with a local medical response unit (e.g., a nurse's station) (118, FIG. 1), then the medical emergency interface 236 will interface directly with the local medical response unit 118 to issue an alert (including the location of the user) to the nurse's station when the user presses the emergency button. In such a situation, the interactive media device 220 supplements an already existing medical response unit, because in many situations, the remote control may be closer to the user than a dedicated, wired emergency button, so the user may issue the alert quicker and easier in an emergency.

In a first example configuration, the medical emergency interface 236 is electronically operative to issue an alert by sending the alert to a local emergency response device such as the local medical response unit 118 (FIG. 1) via a wired connection. Alternatively, the medical emergency interface 236 is electronically operative to issue the alert by sending the alert to the local emergency response device via a wireless connection. Regardless of whether wired or wireless, in an example configuration, the medical emergency interface 236 is electrically operative to issue the alert by sending the alert to a remote emergency response device over the Internet via the network interface.

As another example, if the interactive media device 220 is located in a residential home, then the medical emergency interface 236 may use the network interface 238, the telephone interface 240, a combination of interfaces within the interactive media device 220, etc., to issue the alert to one or more remote medical response units (e.g., a device of an emergency response team, a hospital, a device of a person to be reached in case of emergency, etc.).

Network Interface

The network interface 238 includes hardware that serves as a bridge from the controller 242 and other interfaces of the interactive media device 220 to a network, e.g., network 104 (FIG. 1). In this regard, the network interface 238 performs network traffic processing. As such, the network interface 238 can be used by any component of the interactive media device 220 that need access to a network, e.g., the Internet.

This communication pathway can run bi-directionally, e.g., allowing the media service provider 114 of FIG. 1 to remote log into the interactive media device 120, 220 to set up, program, update, modify or otherwise perform maintenance, improvements upgrades, downgrades, etc., to the capabilities of the interactive media device 120.

Telephone Interface

The telephone interface 240 includes hardware that communicates with the controller 242. Moreover, the telephone interface 240 includes hardware that converts and translates information processed by the controller 242 and external telephony components, e.g., by coupling to a telephone system (landline, cellular, or both) to transmit and receive data. Thus, the telephone interface 240 may communicate with telephones 128 (FIG. 1), an internet to phone bridge 108 (FIG. 1), other telephony devices, an intercom, combinations thereof, etc. For example, when a call is received, the telephone interface 240 may decode a caller ID portion of the call. The controller 242 then coordinates with the television interface 232 to cause the television interface to override a portion of the signal to the television to display the caller ID on the screen. Further, the telephone interface 240 may include a voicemail repository that provides a transcript of the voicemail for users that may be hearing impaired. Once the user accesses the voicemail, the television interface 232 displays the transcript while the voicemail is being played.

Moreover, when a user makes an outgoing call, the telephone interface 240 may detect an encoded pattern (e.g., *123) and route the outgoing call based on the pattern, similar to a speed dial function.

The Controller

The controller 242 includes a processor coupled to memory. The memory can cause the processor to execute program code to carry out the functions described more fully herein. The controller 242 can also interact with local memory to store user interactions with the interactive media device 220, e.g., to record button presses, store channels viewed, times viewed, store a viewing history of interactions across the network 104, discover whether there are static channels, etc. Such information can periodically be communicated to the media service provider 114.

Figure 3:
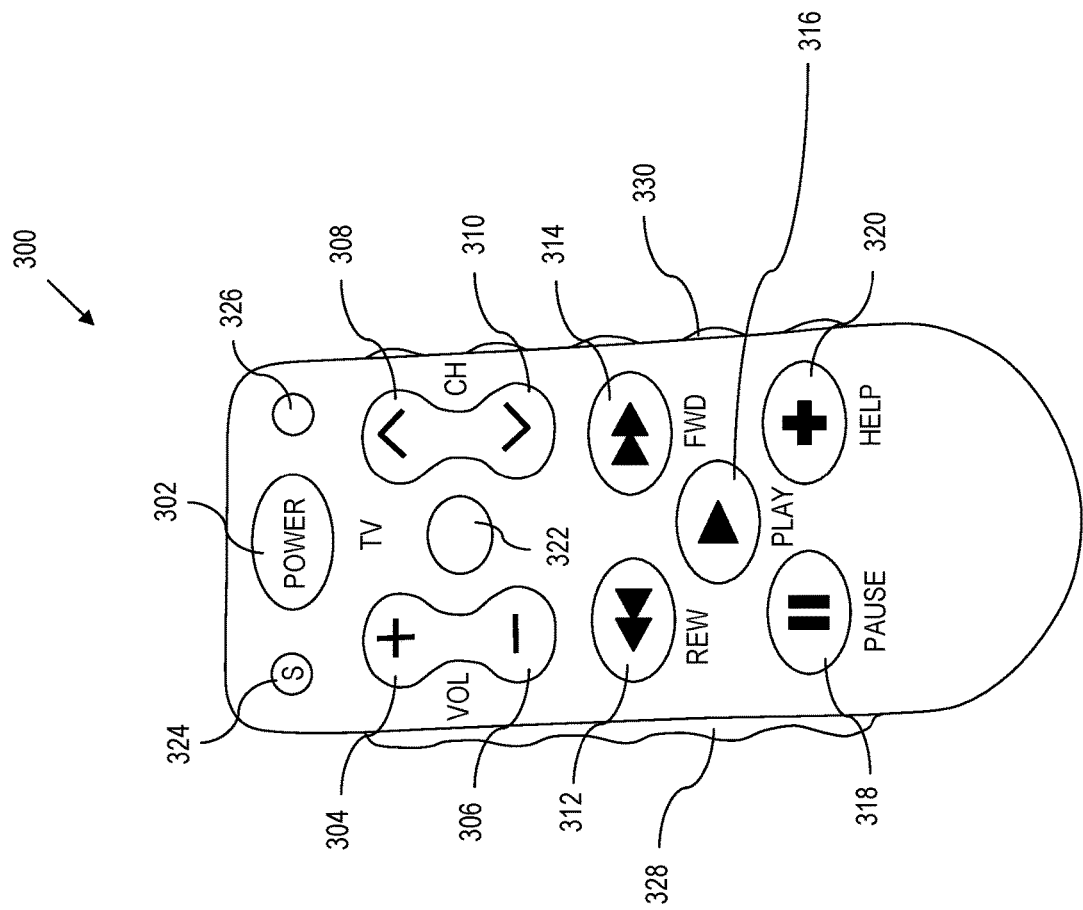
FIG. 3 illustrates an exemplary remote control for interacting with the interactive media device of FIG. 2, according to aspects of the present disclosure herein.

Example Remote Control:

Turning now to FIG. 3, an embodiment of a remote control 300 (equivalent to the remote control 124 of the interactive media system 130 of FIG. 1), with less buttons than a standard remote control is shown. The simplified remote control 300 includes a power button 302, up and down volume control buttons 304, 306, up and down channel buttons 308, 310, and simple DVR buttons: rewind 312, forward 314, play 316, and pause 318.

In addition, the simplified remote control 300 includes an emergency (i.e., "Help") button 320. Notably, residents at a retirement community usually have access to Ecall systems via pull cords and or pendants. However, if the individual needs emergency assistance, that individual either need to be wearing their pendant (many take them off and leave them elsewhere) or they have to be near a pull cord. The pullcords are typically located in a bath room or bed room. So in the case of an emergency, if the individual is not near the pull cord, that individual would have to crawl to the pull cord to pull it.

Also, many residents spend time in their apartments watching television. When they are watching TV, their remote is nearby. If an individual needs emergency assistance while watching TV, the individual does not have to go find their pendant or crawl to a pull cord if using the systems herein. Rather, the individual can just press the emergency button on their remote which will summons emergency assistance.

The remote control also includes a menu button 322 so the user may access menus of the device (220 FIG. 2). For instance, the menu button 322 can be utilized to access the graphical user interface, e.g., implemented by the controller 242 of the interactive media device 220, described with reference to FIG. 1 and FIG. 2. Once the graphical user interface is launched on the television screen, the user can use the remote control to navigate the features of the graphical user interface. The remote control yet further can include a synchronization button 324 that is used to synchronize the remote control 300 with the interactive media device (220, FIG. 2) and learn functionality of buttons on other remote controls (associated and/or not associated with the system 130). As indicated above, when a user presses any of the buttons on the remote control, a wireless signal is sent to the interactive media device, where the signal is received by the remote control interface and decoded.

Further, the simplified remote includes an indication light-emitting diode (LED) 326 that flashes whenever the user has pressed any button. Moreover, each side of the remote control 300 includes a gripping mechanism 328, 330 that makes the simplified remote control 300 easier to grip.

As such, the remote control 300 has fewer buttons than standard remote controls, yet provides the functionality expected by typical users. The remote control 300 is easy to hold due to the relatively smaller form factor enjoyed because of the reduced number of buttons. The remote control 300 also includes easy grip features on each side of the remote control 300.

By facilitating tight coupling between the media service provider 114 and the interactive media device 120, 220, a user can get the functionality of the remote programmed for them without programming themselves. For instance, by dialing a preset number on the telephone 128, or by otherwise contacting the media service provider 114, the media service provider 114 can program the remote control functionality for the user. Moreover, a concierge service provided by the media service provider 114 can facilitate programming for the user so that the user is removed from the technical implementation details of programming. This frees the user to enjoy the use of the interactive media device 120 without understanding how to program it.

Figure 4:
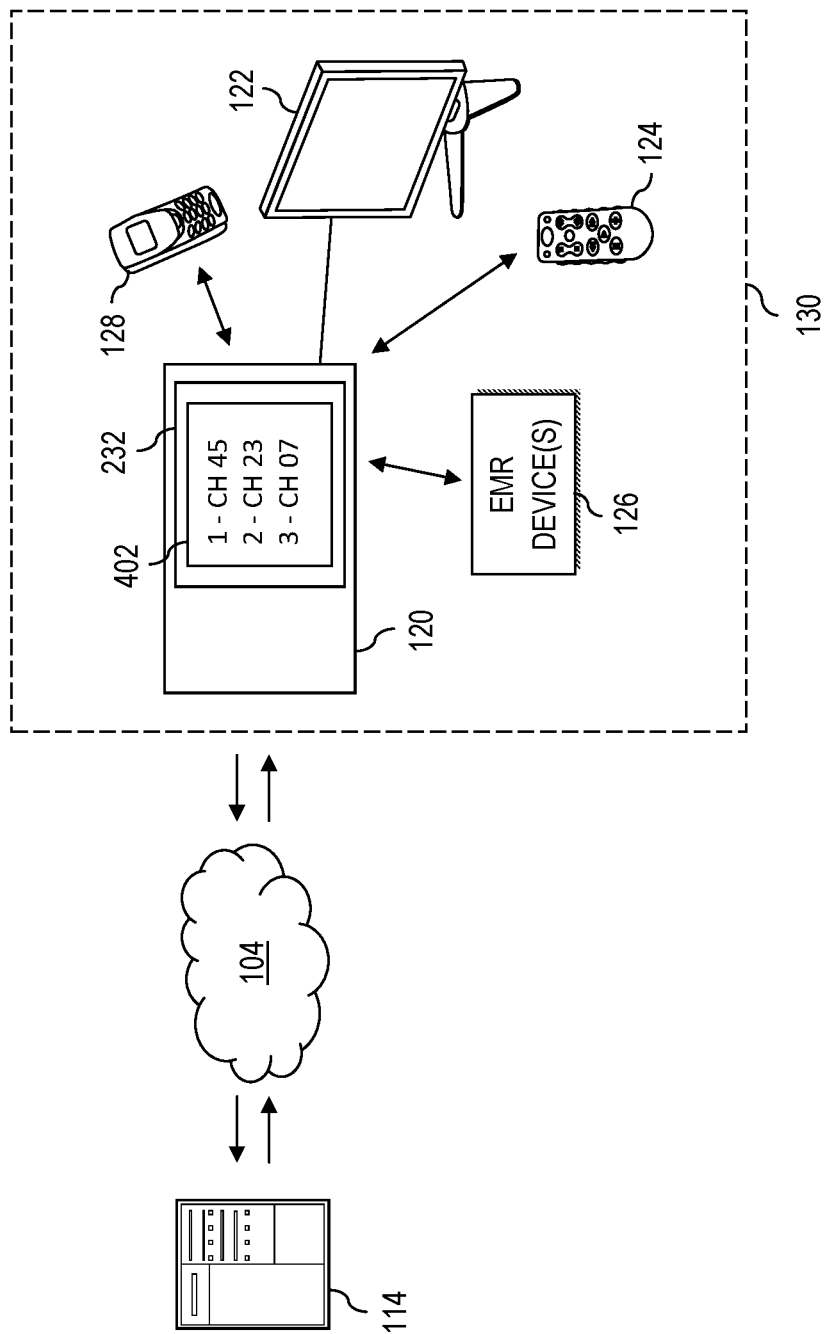
FIG. 4 illustrates a computer-implemented process of programming a remote control for interaction with the interactive media device of FIG. 2, according to aspects of the present disclosure herein.

Example Favorites Setup:

FIG. 4 illustrates how the favorite channels are set up within the television interface of the interactive media device 120, 220 (FIG. 1 and FIG. 2). Basically, a user calls a remote customer service agent via the telephone 128 or any other telephone, or via on-line interaction, and indicates which channels should be included in a set of favorite channels. The customer service agent enters the set of favorite channels for the user to be stored in the user's interactive media device 120, 220. Then the media service provider 114 sends the favorite channels to the interactive media device 120 through the network 104 to the network interface 222, so the favorite channels may be stored in the interactive media device for access by the television interface 232, e.g., via a list or lookup table 402. Creating a set of favorite channels allows a user to navigate a small number of channels without a requirement for numbered buttons on the remote control, so the user does not need to spend time navigating through channels that the user does not care about. For example, referring to FIGS. 1-4 generally, assume a user is watching television channel 45. The user pushes the channel up button 308 (FIG. 3) on the remote 300 (FIG. 3) (or remote 124 of FIG. 1) and the television channel changes directly to channel 23. If the user pushes the channel up button 308 on the remote again, the television channel changes directly to channel 7. If the user pushes the channel up button 308 on the remote yet again, the television channel changes directly to channel 45. Thus, the table 402 creates a rolling queue of channel options pre-selected by the user. The ability to have the buttons of the remote customized and customized on behalf of the user by a remote server is especially convenient for those that have difficulty with technology, e.g., elderly, impaired, handicapped, temporarily disabled persons, etc.

Computer System Overview

Figure 5:
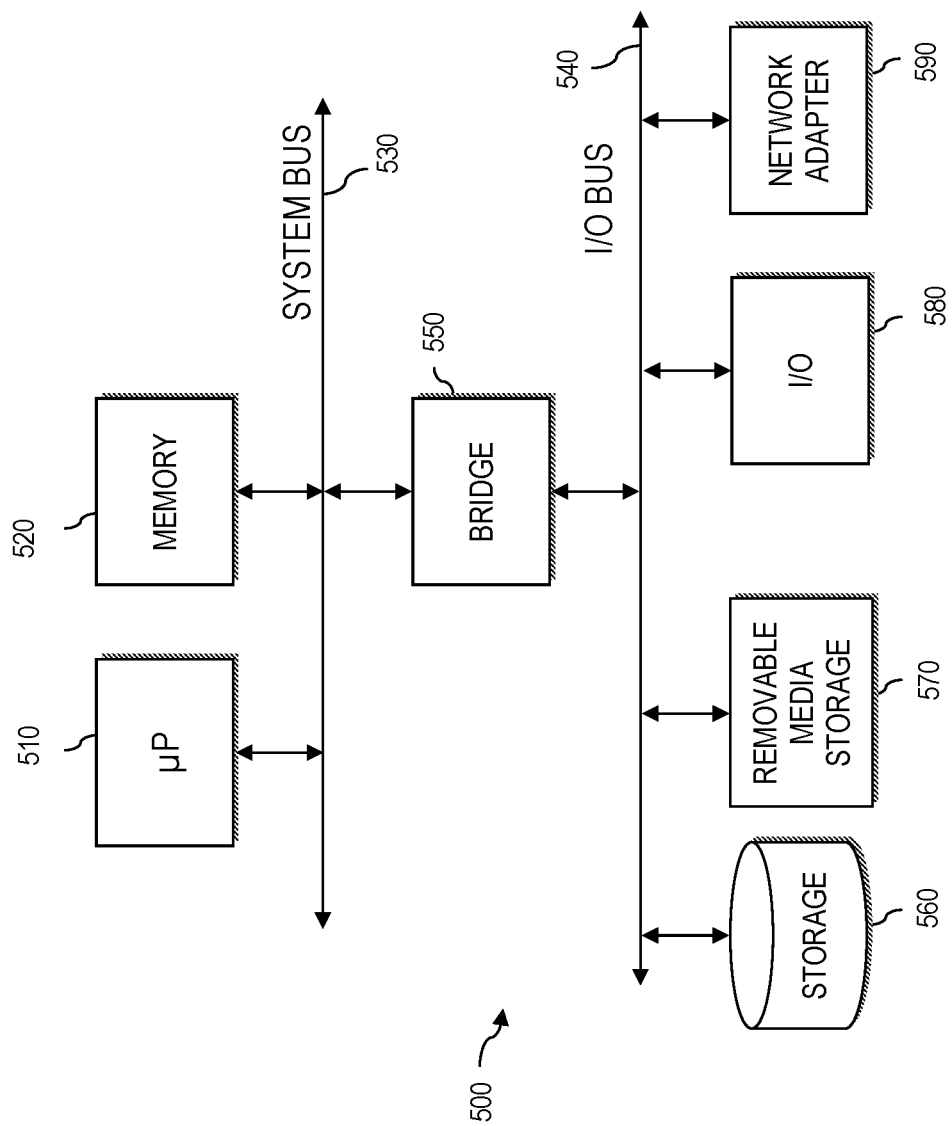
FIG. 5 is a block diagram of a computer processing system capable of implementing any of the systems, computer-implemented processes, or subsets thereof, as described more fully herein.

Referring to FIG. 5, a schematic block diagram illustrates an exemplary computer system 500 for implementing the various processes described herein. For instance, the computer system 500 (or select components thereof) can be integrated into the controller 242 of FIG. 2.

The exemplary computer system 500 includes one or more (hardware) microprocessors (μP) 510 and corresponding (hardware) memory 520 (e.g., random access memory and/or read only memory) that are connected to a system bus 530. Information can be passed between the system bus 530 and bus 540 by a suitable bridge 550. The bus 540 is used to interface peripherals with the one or more microprocessors (μP) 510, such as storage 560 (e.g., hard disk drives); removable media storage devices 570 (e.g., flash drives, DVD-ROM drives, CD-ROM drives, floppy drives, etc.); I/O devices 580 (e.g., mouse, keyboard, monitor, printer, scanner, etc.).

The illustrated network adapter 590 can implement the network interface 238 (FIG. 2) or serve as a connection bridge to a separate hardware implementing the network interface 238.

The above list of peripherals is presented by way of illustration, and is not intended to be limiting. Other peripheral devices may be suitably integrated into the computer system 500.

The microprocessor(s) 510 control operation of the exemplary computer system 500. Moreover, one or more of the microprocessor(s) 510 execute computer readable code that instructs the microprocessor(s) 510 to implement the computer-implemented processes herein. The computer readable code may be stored for instance, in the memory 520, storage 560, removable media storage device 570 or other suitable tangible storage medium accessible by the microprocessor(s) 510. The memory 520 can also function as a working memory, e.g., to store data, an operating system, etc.

The processes herein may be implemented as a machine-executable process executed on a computer system, e.g., one or more of the processing devices 102 of FIG. 1, the controller 242 of the interactive media device 220 (FIG. 2), combinations thereof, etc. Processes herein can also be implemented, at least in part, on a particular computing device such as the interactive media device 220 described with reference to FIG. 1 and FIG. 2. In this regard, the processes herein may be implemented on a computer-readable storage device (e.g., computer-readable storage hardware) that stores machine-executable program code, where the program code instructs a processor to implement the described process. The processes herein may also be executed by a processor coupled to memory, where the processor is programmed by program code stored in the memory, to perform the described method.

In implementing computer aspects of the present disclosure, any combination of computer-readable medium may be utilized. The computer-readable medium may be a computer readable signal medium, a computer-readable storage medium, or a combination thereof. Moreover, a computer-readable storage medium may be implemented in practice as one or more distinct mediums.

A computer-readable signal medium is a transitory propagating signal per se. More specifically, a computer-readable signal medium does not encompass a computer-readable storage medium.

A computer-readable storage medium is a tangible device/hardware that can retain and store a program (instructions) for use by or in connection with an instruction execution system, apparatus, or device, e.g., a computer or other processing device set out more fully herein. Notably, a computer-readable storage medium does not encompass a computer-readable signal medium. Thus, a computer readable storage medium, as used herein, is not to be construed as being transitory signals per se, such as radio waves or other freely propagating electromagnetic waves through a transmission media.

Specific examples (a non-exhaustive list) of the computer-readable storage medium include the following: a hard disk, a random access memory (RAM), a read-only memory (ROM), an erasable programmable read-only memory (EPROM), Flash memory, a portable computer storage device, an optical storage device such as a compact disc read-only memory (CD-ROM) or digital video disk (DVD), or any suitable combination of the foregoing. In particular, a computer-readable storage medium includes computer-readable hardware such as a computer-readable storage device, e.g., memory. Here, a computer-readable storage device and computer-readable hardware are physical, tangible implementations that are non-transitory.

By non-transitory, it is meant that, unlike a transitory propagating signal per se, the contents of the computer-readable storage device or computer-readable hardware that define the claimed subject matter persists until acted upon by an external action. For instance, program code loaded into random access memory (RAM) is deemed non-transitory in that the content will persist until acted upon, e.g., by removing power, by overwriting, deleting, modifying, etc.

Moreover, since hardware comprises physical element(s) or component(s) of a corresponding computer system, hardware does not encompass software, per se.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the invention in the form disclosed. Many modifications and variations will be apparent to those of ordinary skill in the art without departing from the scope and spirit of the invention.

Having thus described the invention of the present application in detail and by reference to embodiments thereof, it will be apparent that modifications and variations are possible without departing from the scope of the invention defined in the appended claims.

What is claimed is:

1. A device comprising:
   a remote control interface that receives wirelessly transmitted signals from a corresponding remote control, the remote control interface configured to receive:
      a first wireless command issued from the remote control in response to a user selection of an emergency button on the remote control;
      a second wireless command issued from the remote control in response to the user selection of at least one television station selection button on the remote control;
   a medical emergency interface that issues an alert over a network to a medical response unit, where the alert is issued responsive to receipt of the first wireless command by the remote control interface;
   a television interface that issues instructions to an associated television receiver to select a channel according to previously programmed favorite channel options, responsive to receipt of the second wireless command by the remote control interface; and
   a network interface that communicably couples the device to a remote media service provider via a network, wherein the network interface enables the remote media service provider to program customized functionality of the alert by the medical emergency interface and customized television channel options of the television interface of the device on behalf of a user that is incapable of programming functionality of the device independently.

2. The device of claim 1, wherein the medical emergency interface is electronically operative to issue the alert by sending the alert to a local emergency response device via a wired connection.

3. The device of claim 1, wherein the medical emergency interface is electronically operative to issue the alert by sending the alert to a local emergency response device via a wireless connection.

4. The device of claim 1 further comprising a controller and a monitor interface electronically connected to the controller, wherein:
   the monitor interface receives a message via the network interface; and
   the television interface overrides the content on the screen of the television to display the message on the screen of the television.

5. The device of claim 4, wherein the medical emergency interface is electrically operative to issue the alert by sending the alert to a remote emergency response device over the Internet via the network interface.

6. The device of claim 4, wherein the monitor interface couples to an emergency medical record repository so as to be able to access medical records associated with the user.

7. The device of claim 6, wherein:
   the monitor interface receives a medical record from the emergency medical record repository via the network interface; and
   the television interface overrides the content on the screen of the television to display the record on the screen of the television.

8. The device of claim 6, wherein the monitor interface:
   electronically couples to at least one local medical device;
   receives medical information about the user via at least one local medical device; and
   sends the medical information about the user to the emergency medical record repository via the network interface.

9. The device of claim 1, wherein the television interface is further programmed to include a subset of available channels to allow the user to skip unwanted channels.

10. The device of claim 1 further comprising a controller and a wired telephone interface electronically connected to the controller, the wired telephone interface integrating telephone communication though the device.

11. The device of claim 1 further comprising a controller and a cellular telephone interface electronically connected to the controller, the cellular telephone interface integrating telephone communication though the device.

12. The device of claim 1 further comprising a controller, wherein:
   the controller further implements a graphical user interface for the display of information on the screen of the associated television, the graphical user interface configured to provide a graphical version of the emergency button on the remote control, which when virtually actuated, causes the controller to issue an alert through the medical emergency interface.

13. A device comprising:
   a remote control interface that receives wirelessly transmitted signals from a corresponding remote control, the remote control interface configured to receive:

a first wireless command issued from the remote control in response to a user selection of an emergency button on the remote control;
a second wireless command issued from the remote control in response to the user selection of at least one television station selection button on the remote control;
a medical emergency interface that issues an alert over the network to a medical response unit, where the alert is issued responsive to receipt of the first wireless command by the remote control interface;
a television interface that issues instructions to an associated television receiver to select a channel according to previously programmed favorite channel options, responsive to receipt of the second wireless command by the remote control interface;
a network interface that communicably couples the device to a remote media service provider via a network, wherein the network interface enables the remote media service provider to program customized functionality of the device for the user, including programming the alert and programming the favorite channel options on behalf of a user that is incapable of programming functionality of the device independently;
a monitor interface that electronically communicates across the network via the network interface; and
a controller connected to the remote control interface, the medical emergency interface, the television interface, the network interface, and the monitor interface, to control operation of the device.

14. The device of claim 13, wherein the monitor interface:
electronically communicates with a local medical device;
receives medical information about the user via the local medical device; and
sends the medical information about the user to an emergency medical record repository.

15. The device of claim 14, wherein the monitor interface sends the medical information about the user to the emergency medical record repository via the network interface.

16. The device of claim 13, wherein:
the monitor interface receives a message via the network interface; and
the television interface overrides the content on the screen of the television to display the message on the screen of the television.

17. The device of claim 16, wherein the message comprises a medical record that the monitor interface receives from an emergency medical record repository via the network interface.

18. The device of claim 16, wherein:
the received medical record indicates that the user should perform a task;
the television interface overrides the television to display the task on the television; and
the monitor interface sends an indication to the emergency medical record repository that the task has been completed based on feedback from the user.

19. The device of claim 16, wherein:
the monitor interface couples to a local medical device;
the received medical record indicates that the user should perform a task using the local medical device;
the television interface overrides the television to display the task on the television; and
the monitor interface sends an indication to the emergency medical record repository that the task has been completed based on feedback from the local medical device.

20. A device comprising:
a remote control interface that receives a wireless signal from a corresponding remote control, the remote control having an emergency button that upon actuation, causes the remote control to issue a first wireless command as the wireless signal;
a controller electronically connected to the remote control interface, where the controller decodes a representation of the wireless signal received by the remote control interface to determine select one of:
whether a user has pressed the emergency button by identifying the first wireless command; and
whether a user has pressed a button of the remote control to control an associated television;
a television interface electronically connected to the controller, where the television interface issues an instruction to the associated television in response to the controller determining that the user has pressed a button of the remote control to control the associated television, wherein the instruction is based on a translation of the wireless signal to a corresponding television adjustment command;
a medical emergency interface electronically connected to the controller, where the medical emergency interface issues an alert in response to the controller determining that the user has pressed the emergency button; and
a network interface that communicably couples the device to a remote media service provider via a network, wherein the network interface enables a remote media service provider to access the device and program customized functions of the device on behalf of the user that is incapable of programming functionality of the device independently.

* * * * *